United States Patent

Junginger et al.

[11] 3,976,052
[45] Aug. 24, 1976

[54] RESPIRATION MONITOR

[75] Inventors: Gerhard Junginger, Holzgerlingen; Helmut Zeeb, Kirchentellinsfurt, both of Germany

[73] Assignee: Hewlett-Packard GmbH, Wurttemberg, Germany

[22] Filed: Jan. 10, 1975

[21] Appl. No.: 540,038

[30] Foreign Application Priority Data
Apr. 19, 1974 Germany............................ 2418910

[52] U.S. Cl. ......................... 128/2.1 Z; 128/2.05 R; 128/DIG. 29
[51] Int. Cl.²............................................ A61B 5/08
[58] Field of Search ............. 128/2.1 Z, 2.1 R, 2 R, 128/2.05 V, 2.05 R, 2.06 R, 2.08, DIG. 29

[56] References Cited
UNITED STATES PATENTS 3,572,317  3/1971  Wade........................... 128/DIG. 29
3,871,360  3/1975  Horn............................... 128/2.1 Z Primary Examiner—Robert W. Michell
Assistant Examiner—Lee S. Cohen
Attorney, Agent, or Firm—Stephen P. Fox

[57] ABSTRACT

A respiration monitor for measuring the variations of the thorax impedance of a patient due to respiration activity includes circuitry for suppressing the indication of unwanted signals caused by the activity of the heart. This circuitry is connected to receive separate signals corresponding to the heart beat rate and compare the periods of these signals to those of the signals measured at the thorax of the monitored person. If the periods of both signals are substantially equal, i.e. the signals measured at the thorax are actually due to heart activity rather than to respiration, the trigger threshold value of the monitor is automatically and stepwise raised so that the monitor does no longer respond to heart beat related signals but indicates that no respiration signals are measured.

7 Claims, 3 Drawing Figures

RESPIRATION MONITOR

BACKGROUND OF THE INVENTION

This invention relates to a respiration monitor, in which the respiration activity is monitored by measuring the variations of the thorax impedance of a patient caused by his respiration activity. The monitor includes means for suppressing the indication of disturbing signals, especially those, which are introduced by the heart beat activity, which have amplitudes below a certain threshold value. This threshold value is adjusted to correspond to a predetermined fraction of the amplitude of the measuring signal which corresponds to the respiration activity.

Respiration monitors of this kind are used for monitoring patients especially in intensive care stations. They measure the respiration frequency of the patient, record the respiration curve and indicate respiration irregularities, especially a stand still of the respiration activity (apnea). The impedance variations in the thorax region caused by the heart activity are obscured by interfering influences which are primarily introduced by the heart activity. Not only the respiration activity but also the heart activity result in a periodical change of the thorax impedance, but the amplitude of the impedance variation caused by heart activity is usually substantially smaller than the impedance variation caused by respiration. However, the heart beat frequency is generally higher than the respiration frequency.

In order to suppress disturbances, some known monitors feed the electrical signals obtained by a variation of the thorax impedance to a trigger circuit, which will only deliver an output signal when the amplitude of the supplied input signal exceeds a predetermined threshold value. This threshold value is manually adjustable and is selected so that it is lower than the amplitude of the signals derived by the respiration activity and that it is higher than the amplitude of the signals caused by the heart activity. The disadvantage of this type of respiration monitors is that the threshold value has to be readjusted frequently, as the amplitudes of the respiration signals do not only differ from patient to patient, but may also differ with the same patient over an extended time interval. An additional difficulty is that the threshold value cannot be adjusted accurately, as the periodic impedance variations due to heart activity are generally exceeded by those caused by respiration activity.

In order to avoid such manual readjustment of the trigger threshold, a known type of respiration monitor is provided with a trigger level controller, which automatically adjusts the threshold value to a certain fraction, for example to two thirds, of the actual amplitude of the respiration signal. The readjustment occurs with a certain delay so that it will be primarily influenced by respiration signals having a high amplitude, while it tends not to be influenced by interfering signals which occur between those high amplitude signals.

Furthermore, a lower limit is provided for the threshold value, which is higher than the lowest amplitudes of the respiration signals. However, this lower limit should be higher than the highest possible amplitude of the heart beat signals. In practice, these two requirements can hardly be met simultaneously, as the amplitude of the respiration signals may be equal or smaller than that of the signals introduced by the heart activity. If the lower limit for the threshold value is made as high that it is above the amplitude of the heart signals in all cases, it may happen that the respiration monitor does not respond to weak respiration signals. If the lower limit for the threshold value is low enough for weak respiration signals, the automatic readjustment may fail, if a respiration stand still (apnea) occurs or if the amplitude of the respiration signals is not substantially higher than that of the heart signals. In these cases there will result a threshold value which has a lower amplitude than the heart signals, so that the trigger circuit supplies output signals which are caused by heart activity and which will thus result in wrong indication of the respiration activity. Especially if a respiration stand still will occur, the observer will get the wrong impression of respiration activity.

SUMMARY OF THE INVENTION

It is the object of this invention to provide a respiration monitor which will not be responsive to disturbing signals caused by the activity of the heart, even in case the amplitudes of the disturbing signals are equal or greater than the amplitudes of the respiration signals or in case no respiration signals are present at all.

According to this invention this object is solved in that the respiration monitor is set up to simultaneously receive signals related to the heart beat rate of the same patient and that it comprises a period comparator which compares the duration of the heart beat related signal period to that of the respiration related signal period. In case both periods are substantially of the same duration, the comparator will supply a signal to a device for suppressing disturbing signals so that the trigger threshold of the monitor will be raised by a certain amount. Thus, it will be prevented that signals which are related to the activity of the heart are erroneously taken for respiration signals, even if no respiration signals are present at all. Naturally, in this case the signals measured at the thorax have at least approximately equal periods as the signals related to heart activity. The resulting raise of the trigger threshold prevents the indication or recording of such disturbing signals so that a respiration stand still can be safely detected. As on the other hand the respiration and heart frequencies will generally be distinctly different from each other, the comparator will not be responsive as long as there is a sufficiently strong respiration activity.

DESCRIPTION OF A PREFERRED EMBODIMENT

Figure 1:
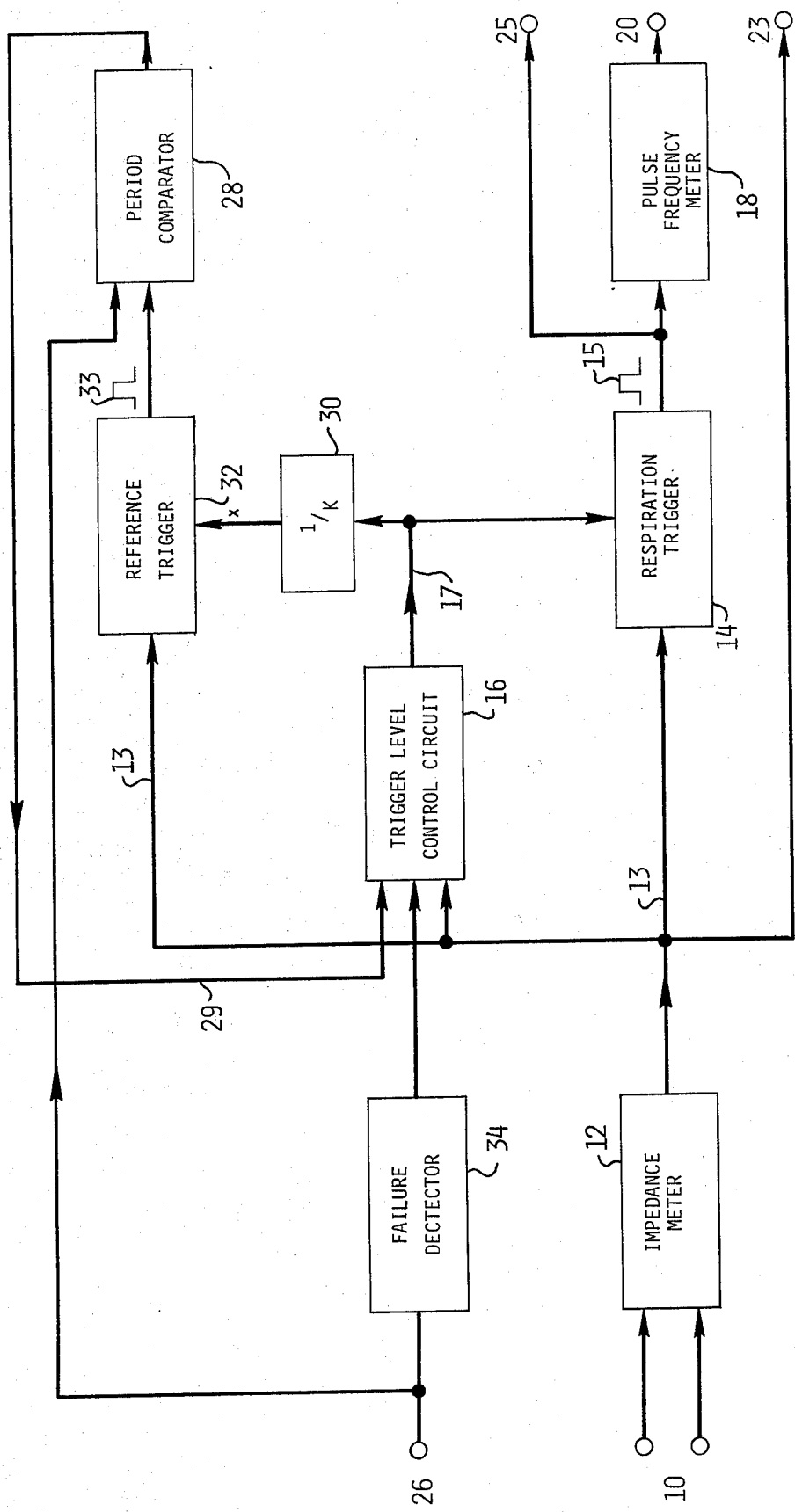
FIG. 1 is a block diagram of a respiration monitor according to a preferred embodiment of the invention.

FIG. 1 shows a block diagram of a respiration monitor according to a preferred embodiment of the invention. The illustrated respiration monitor includes an input 10 which can be connected to two electrodes (not shown). These electrodes should be mounted on the thorax of the patient in spaced relationship. The input 10 is connected to an impedance meter 12 which supplies an output signal 13 corresponding to the thorax impedance between the electrodes. This signal varies with inhaling and exhaling and thus is a measure for the respiration activity of the patient. The impedance meter 12 may preferably comprise an impedance measuring bridge operated at 65 kHz as well as a demodulator and amplifier. The basic impedance of the thorax is not taken into consideration, but only the impedance variations are measured. It should be noted that such impedance meters are well known to those skilled in the art.

The output signal 13 of the impedance meter 12 is supplied to a respiration trigger circuit 14, which will deliver an output pulse 15 each time a certain amplitude value is exceeded. A detailed description of the trigger circuit 14 is included in the Hewlett-Packard Operating and Service manual of Respiration Module 78202 A/B, January 1973. The output pulses 15 are on the one hand immediately supplied to an output 25 which may be connected to a control light which will flash upon each respiration cycle. There can also be connected a monitoring means to the output 25 to deliver an alarm signal in case a certain time interval has lapsed after a respiration pulse 15 without the occurrence of another pulse 15, i.e. in case a respiration still stand has occurred.

The output pulses 15 of the respiration trigger circuit 14 are also supplied to a pulse frequency meter 18 which will feed a signal to the output 20, which signal is proportional to the respiration frequency. For recording purposes there is provided another output 23 where the output signal of the impedance meter 12 can be obtained directly.

The minimum amplitude, at which the respiration trigger circuit 14 supplies an output pulse 15, is determined by the output voltage signal 17 supplied to the respiration trigger circuit 14 by a trigger level control circuit 16. The output signal 13 of the impedance meter 12 is also one of the input signals for the trigger level control circuit 16. The average value of the signal 17 is proportional to the amplitude of the signal 13, but the signal 17 will follow the signal 13 with a certain delay. With increasing amplitude of the signal 13 the time constant $\tau_1$ of this delay will be in the range of the period of the signal 13, while the time constant $\tau_2$ with a falling amplitude of the signal 13 is a multiple of the period of the signal 13. It has been proved suitable to adjust the minimum amplitude, i.e. the threshold value, always to two thirds of the amplitude of the signal 13 in this manner. A more detailed description of the trigger level control circuit 16 is given later on.

A reference trigger circuit 32 which is substantially equal to the respiration trigger circuit 14, is also supplied with the output signal 13 of the impedance meter 12 and delivers pulses 33, when the amplitude of signal 13 exceeds a certain threshold value. This threshold value is also determined by the output signal 17 of the trigger level control circuit 16. However, it is smaller than the threshold value of the espiration trigger circuit 14 by a factor of K. This is achieved in that the signal 17 is fed to the reference trigger circuit 32 via an attenuator 30 which supplies a signal corresponding to the signal 17 but divided by K. The output pulses 33 of the reference trigger circuit 32 are supplied to a period comparator 28. The period comparator 28 also receives a signal via a further input 26 of the respiration monitor, which signal corresponds to the heart period of the ECG of the patient. This signal delivered to the input 26 can for example be taken from a usual ECG monitor connected to the patient and is preferably a DC voltage proportional to the heart rate (heart beat frequency). The period comparator 28 compares the period represented by its inputs and delivers an output signal 29 to the trigger level controller 16, when the periods are substantially equal. It has been found suitable to set up the period comparator 28 so that it will deliver an output signal 29, when the two periods will not differ from each other by more than 15 percent. The period comparator will be described later on in more detail. The trigger level controller 16 raises its output signal 17 by a certain amount if the signal 29 is present. Thus, the respiration trigger circuit 14 and the reference trigger circuit 32 will become less sensitive If the signal 29 will subsequently occur again, the signal 17 will be further raised. This will happen as long as no pulse 33 and thus no signal 29 will occur. The signal 17 will drop according to the time constant $\tau_2$ until the reference trigger circuit 32 will become responsive again and the period comparator 28 will deliver another signal 29 for raising the signal 17, provided the periods of the compared signals are still substantially equal. As long as the periods represented by the compared signals are substantially equal the signal 17 being divided by K will have an average value which corresponds to the amplitude of the signal 13. Thus it is made sure that the respiration trigger circuit 14, which is K times less sensitive than the respiration trigger circuit 32, will not deliver pulses 15 as long as the periods are equal.

When the reference trigger circuit 32 is supplied with a signal 13 being divided by K, it will already be responsive to lower amplitudes of the signal 13 than the respiration trigger circuit 14. Thereby it is made sure that the period comparator 28 will become responsive early in time and will deliver an output signal 29 for raising the output signal 17 of the trigger level controller 16 before the signal 17, in the case of small amplitudes of the output signal 13 of the impedance meter 12, has dropped to a value, at which the respiration trigger circuit 14 is already responsive to disturbing signals. On the one hand, the factor K should be great enough in order to effectively prevent that the respiration trigger circuit 14 will respond to disturbing signals. On the other hand it should not have such a value that the reference trigger circuit 32 will already become responsive to the noise which is superposed on the respiration and heart activity signals. A value between 2 and 10 for the factor K has been proved suitable. The optimum vaue for K depends furthermore on the time constant $\tau_2$. The smaller $\tau_2$ is made, i.e. the quicker the signal 17 will follow a drop in amplitude of the signal 13, the higher the factor K should be in order to be able to compare the periods in any case before the respiration trigger circuit 14 has become so sensitive that it will respond to disturbing signals.

Suitably, the trigger level controller 16 includes a limiter which will limit the output signal 17 as to its upper and lower values. In practice it has been proved advisable to select this limitation so that the sensitivity of the respiration trigger circuit 14 does only vary in a region which corresponds to the impedance amplitude of the signal 13 from 0.1 ohms through about 1.5 ohms. Thus, the fact is taken into consideration that amplitudes below 0.1 ohms may physiologically no longer be regarded as respiration related values, while there are disturbing signals with amplitudes above 1.5 ohms. Amplitudes below 0.1 ohms will in no case result to an output pulse 15, while amplitudes above 1.5 ohms will in any case result in an output pulse 15.

The period comparator 28 can only operate as long as it is supplied with a signal related to the heart rate via the input 26. In case this signal will fail because of any reason, no output signal 29 can be delivered, even if the periods of the output signal 13 of the impedance meter 12 and of the signal related to heart beat activity are equal. In this case, the output signal 17 of the trigger level controller 16 would not be raised and the sensitivity of the respiration trigger circuit would be lowered so that it would also deliver output pulses 15 upon disturbing signals. Then an apnea might not be observable. In order to void such a wrong indication, there is provided a signal failure detector 34 which in case of a signal drop out at the input 26 delivers a signal to the trigger level controller 16. When this signal appears, the lower limit of 0.1 ohms is raised to a higher value (e.g. 0.5 ohms) in order to prevent that the respiration trigger circuit 14 is responsive to usual disturbing signals. The signal failure detector 34 may be a simple voltage comparator which compares the heart rate related voltage with a reference voltage corresponding to the minimal possible heart rate, and which delivers a failure signal in case that the heart rate related voltage is below said reference voltage.

Figure 2:
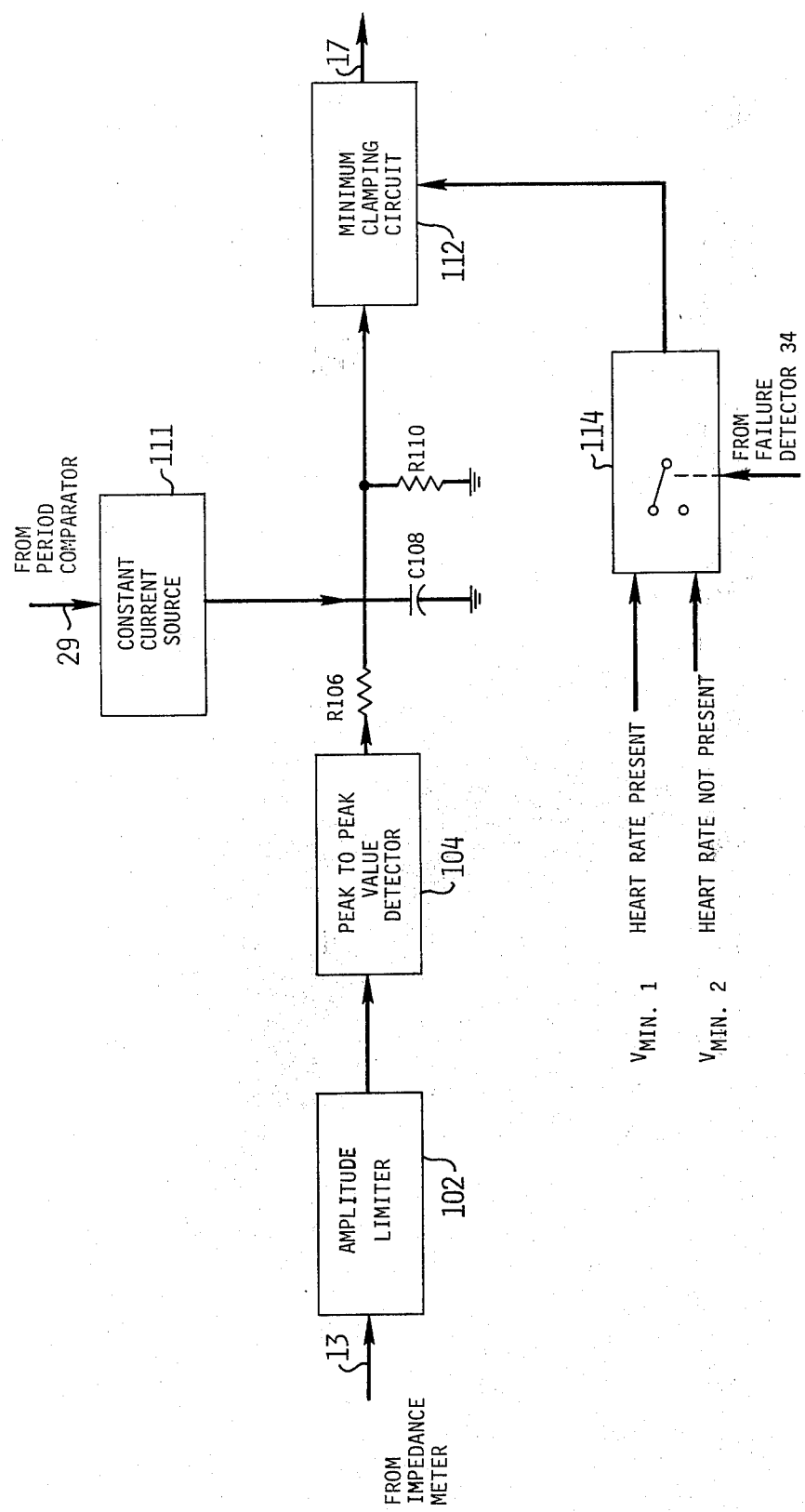
FIG. 2 is a detailed block diagram of the trigger level control circuit included in FIG. 1.

Referring now to FIG. 2 there is shown the trigger level control circuit 16 of FIG. 1 in more detail. Signal 13 from impedance meter 12 is fed via an amplitude limiter 102 to a peak value detector 104. The amplitude limiter 102 limits the amplitudes of signal 13 to a value which is in any case greater than the largest heart signals which may be included in signal 13. The output of peak to peak value detector 104 is a voltage proportional to the amplitude limited peak to peak value of signal 13 and is delivered via a RC-network to a minimum clamping circuit 112. The RC-network consists of resistors R 106, R 110 and capacitor C 108 and causes the above mentioned delays in the signal 17. Time constant $\tau_1$ is determined by resistor R 106 and capacitor C 108, and time constant $\tau_2$ is determined by capacitor C 108 and reistor R 110.

A constant current source 111 charges the capacitor C 108 with constant current as long it is actuated by the signal 29 from the period comparator 28. Signal 17 is thereby raised by a certain amount as described above.

The minimum clamping circuit 112 determines the minimum value of signal 17. This minimum value is selected by a switching device 114 from two different values (heart rate present and heart rate not present respectively) as described above. Switching device 114 is actuated by the output signal of failure detector 34.

Figure 3:
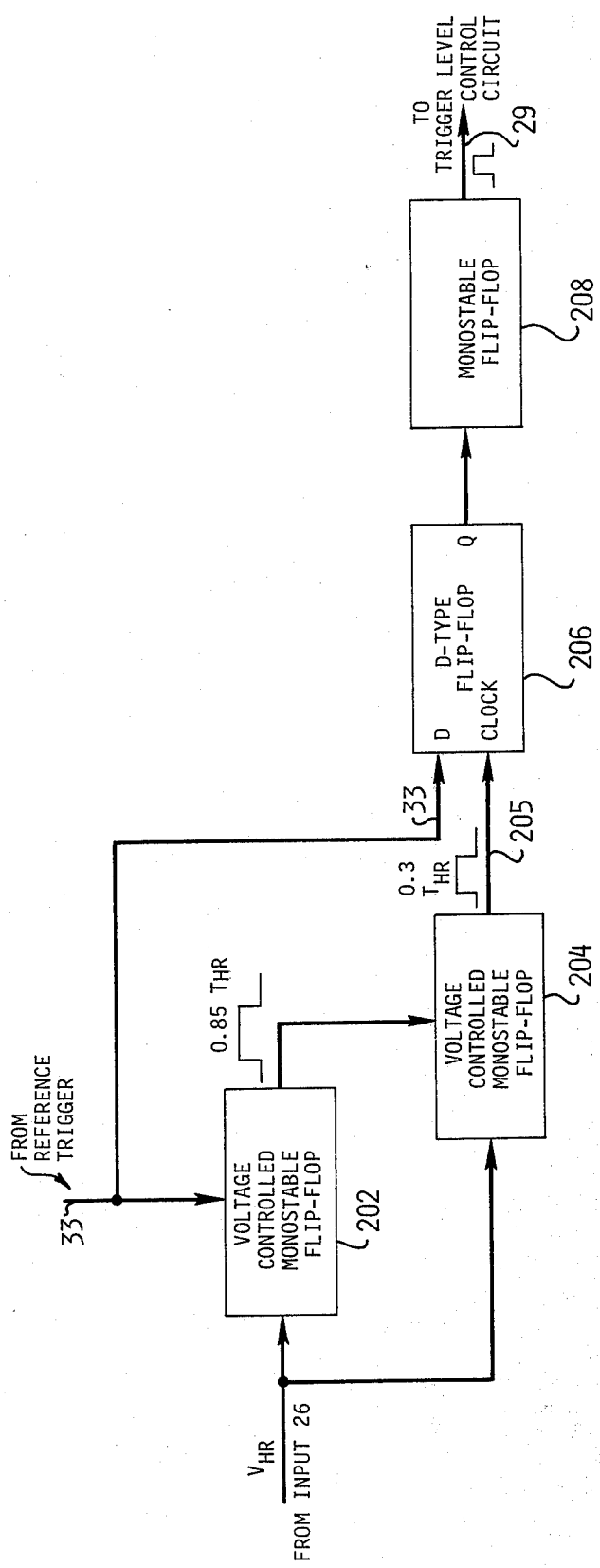
FIG. 3 is a detailed block diagram of the period comparator included in FIG. 1.

FIG. 3 shows the period comparator 28 of FIG. 1 in more detail. The DC voltage signal $V_{HR}$ coming from input 26 and being proportional to the heart rate is fed to two voltage controlled monostable flip-flops 202 and 204. The durations of the output pulses of flip-flops 202 and 204 are inversely proportional to $V_{HR}$, i.e. proportional to the heart beat period $T_{HR}$. The duration of the output pulse of flip-flop 202 is adjusted to 0.85 $T_{HR}$ and the duration of the output pulse 205 of flip-flop 204 is adjusted to 0.3 $T_{HR}$ Every time a pulse 33 from reference trigger 32 is applied to flip-flop 202, an output pulse is produced. These output pulses are applied to flip-flop 204, and upon termination of said output pulse flip-flop 204 produces an output pulse 205. Thus, each output pulse 205 starts at 0.85 $T_{HR}$ and ends at 1.15 $T_{HR}$ after the corresponding pulse 33. The subsequent pulse 33 will therefore occur simultaneously with pulse 205 if the pulse period of signal 33 differs less than 15 percent from $T_{HR}$. If pulses 33 and 205 occur simultaneously a D-type flip-flop 206 generates an output signal on its Q-output. This output signal is fed to a monostable flip-flop 208 which in turn delivers the above mentioned output signal 29 to the trigger level control circuit 16.

We claim:

1. Apparatus for monitoring the respiration activity of a patient and for suppressing disturbing signals comprising:
   first means connectable to a patient for providing a variable thorax impedance signal;
   second means connectable to the patient for providing a heart rate signal;
   trigger level means coupled to said first means for providing an adjustable threshold value, said trigger level means having control input means for raising said threshold value;
   reference trigger means coupled to said trigger level means and said first means for producing a trigger pulse in response to the amplitude of said thorax impedance signal exceeding a level related to said threshold value;
   comparator means coupled to said reference trigger means and said second means for providing an output signal to the control input means of said trigger level means in response to said trigger pulse and said heart rate signal having substantially equal periods, thereby to raise said threshold value; and
   output means coupled to said trigger level means and said first means for producing a respiration signal in response to the amplitude of said thorax impedance signal and said threshold value.

2. The monitoring apparatus of claim 1, wherein said comparator means includes means for providing said output signal when the periods of said trigger pulse and said heart rate signal differ by less than 15 percent.

3. The monitoring apparatus of claim 1 wherein said output means includes respiration trigger means coupled to said trigger level means and said first means for producing a respiration output pulse in response to the amplitude of said thorax impedance signal exceeding said threshold value.

4. The monitoring apparatus of claim 3 wherein said trigger level means includes means for limiting adjustment of said threshold value to a range having a predetermined lower limit above the amplitude of noise signals and a predetermined upper limit above the greatest possible amplitudes of disturbing signals.

5. The monitoring apparatus of claim 4 wherein:
   said second means for providing a heart rate signal includes means for detecting failure of heart activity; and
   said trigger level means responsive to the output of said detecting means for controlling said limiting means to raise said threshold value to said upper limit.

6. The monitoring apparatus of claim 3 wherein said trigger level means includes means for providing delayed adjustment of said threshold value in response to the amplitude of said thorax impedance signal.

7. The monitoring apparatus of claim 6 wherein said means for providing delayed adjustment of said threshold value includes delay network means for providing first and second delays in response to increasing and decreasing amplitudes of said thorax impedance signal, respectively, said first delay being in the range of the period of said thorax impedance signal, and said second delay being a multiple of the period of said thorax impedance signal.

* * * * *

UNITED STATES PATENT AND TRADEMARK OFFICE
CERTIFICATE OF CORRECTION

PATENT NO. : 3,976,052
DATED : August 24, 1976
INVENTOR(S) : Gerhard Junginger and Helmut Zeeb It is certified that error appears in the above—identified patent and that said Letters Patent are hereby corrected as shown below:

Column 4, line 1, "period" should read -- periods --;

Column 5, line 28, "peak value" should read -- peak to peak value --;

Column 6, line 53, "means responsive" should read -- means includes means responsive --.

Signed and Sealed this

Ninth Day of November 1976

[SEAL]

Attest:

RUTH C. MASON
Attesting Officer

C. MARSHALL DANN
Commissioner of Patents and Trademarks